United States Patent [19]

Krener et al.

[11] 3,968,678
[45] July 13, 1976

[54] METHOD OF DETERMINING THE RELATIVE AIR CONTENT IN AN AIR-CONTAINING LIQUID OR CREAM AND AN APPARATUS FOR CARRYING OUT THE METHOD

[75] Inventors: Ole Garne Krener; Erik Nielsen, both of Hojbjerg, Denmark

[73] Assignee: O. G. Hoyer A/S, Aarhus-Hojbjerg, Denmark

[22] Filed: Mar. 27, 1975

[21] Appl. No.: 562,951

[30] Foreign Application Priority Data
Apr. 5, 1974 Denmark............................ 1911/74

[52] U.S. Cl. .................................................. 73/19
[51] Int. Cl.[2]........................................... G01N 7/00
[58] Field of Search .............................. 73/19, 32 R

[56] References Cited
UNITED STATES PATENTS

| | | | |
|---|---|---|---|
| 2,138,141 | 11/1938 | Cromer et al............................ | 73/19 |
| 2,141,977 | 12/1938 | Gray ........................................ | 73/19 |
| 2,736,190 | 2/1956 | Bockelman et al...................... | 73/19 |

*Primary Examiner*—James J. Gill
*Attorney, Agent, or Firm*—Browdy and Neimark

[57] ABSTRACT

A method and an apparatus for determining the relative air or gas content in a product flowing through a conduit. By means of two substantially synchronized pistons moving in opposed cylinders, a sample of the product is transferred from the conduit to a sampling chamber defined in one of the cylinders between the pistons. After the sample has been isolated from the material flowing through the conduit, the pistons are moved towards one another whereby the volume of the sampling chamber is reduced to a predetermined value. The compression of the sample results in an increased pressure, and when the pressure has reached a predetermined value, an overflow valve is opened to let excess material flow from the sampling chamber back to the conduit. When the movement of the pistons towards one another has stopped and said predetermined pressure has been established in the sample, a predetermined expansion of the sample is effected by moving the pistons a predetermined distance from one another. The pressure in the sampling chamber after the expansion has been effected, is then representative of the relative air content in the sample.

10 Claims, 3 Drawing Figures

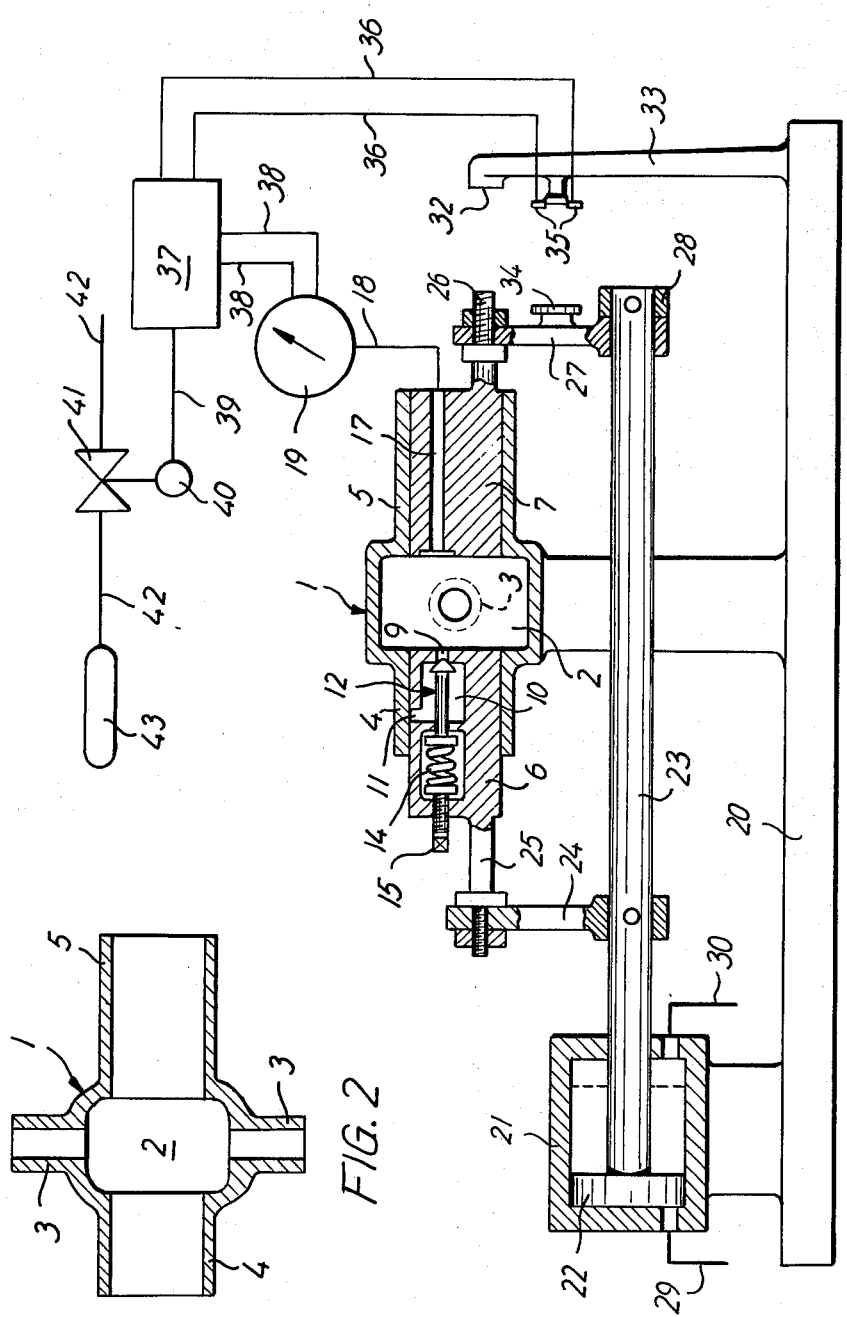

METHOD OF DETERMINING THE RELATIVE AIR CONTENT IN AN AIR-CONTAINING LIQUID OR CREAM AND AN APPARATUS FOR CARRYING OUT THE METHOD

BACKGROUND OF THE INVENTION

This invention relates to a method of determining the relative air content in a product which in the form of an air-containing liquid or cream flows through a conduit. The method includes transferring a sample of the flowing product from the conduit to a sampling chamber which can be isolated from the conduit and which has a variable volume, effecting a predetermined variation of the volume of the chamber and hence of the sample after the chamber has been isolated from the conduit and measuring the pressure in the chamber resulting from the volume variation.

In the industrial production of ice-cream, souffle, pudding and many other products, air or other gas is mixed with or whipped into a liquid initial material having a more or less viscous or stiff consistency, after which the product is pumped through a conduit, usually at a certain positive pressure, to a dispensing station at which it is discharged into containers, for example portion packages for retail sale. For the sake of convenience the term "air" is used herein to designate any gas which may be added to a fluent material for modifying its consistency.

The magnitude of the relative air content, which in the production of ice-cream is also known as the swelling degree, is defined as the ratio between the volume of the quantity of air at atmospheric pressure and the volume of the liquid phase. It is generally of importance for the price of the final product as well as for its quality. In the law, maximum values of the air content of foodstuffs and similar edible products are often laid down, and it is then in the interest of the producer that the quantity of air can be kept as closely as possible below the value permitted.

Normally, the admixture of air is controlled by manually adjusting a reduction valve through which compressed air is introduced into the initial material. The adjustments are effected on the basis of the operator's experience combined with intermittent measurements carried out on the dispensed product. The measurements are generally carried out by withdrawing a sample having a certain volume, for example half a liter, in the dispensing station and weighing the sample. The air content, measured in per cent, can then be determined by comparing the specific gravities of the sample and of the initial material. This measuring method is not very accurate and is rather time-consuming, so that in practice the measurements are carried out only at comparatively long intervals, during which the parameters relevant to the air content, including the composition and temperature of the initial material, may however vary considerably, which further reduces the accuracy of the method. In addition, a comparatively long time elapses before a change in the supply pressure of the air gets any influence on the final product discharged at the dispensing station, and the withdrawal of each sample causes a certain waste which may be considerably larger than the volume of the sample.

It is known to control the air content in ice-cream by supplying compressed air to the liquid mix through a nozzle which operates at the critical pressure ratio so that the flow rate of air through the nozzle depends solely on the pressure upstream of the nozzle. This method requires a comparatively expensive equipment and it requires a high quality of the pumps for transporting the cream. Furthermore, an adjustment of the equipment is necessary every time the output of the ice-cream freezer is varied.

From the specification of U.S. Pat. No. 2,141,977 there is known an apparatus for determining the air content in for example ice-cream. The apparatus is designed as a cock connected to a conduit through which the ice-cream flows. The rotatable plug of the cock contains a sampling chamber through which the cream flows in one position of the plug and which is isolated from the conduit when the plug is rotated 90°. A piston may be pressed into the sampling chamber, whereby the volume of the chamber is reduced and at the same time the pressure rises in the trapped ice-cream sample. The final pressure in the sample depends on the relative air content of the cream.

SUMMARY OF THE INVENTION

According to the invention there is provided a method of determining the relative air content in a product flowing through a conduit in the form of an air containing liquid or cream, comprising the successive steps of a. transferring a sample of said product from said conduit to a closed sampling chamber of variable volume, b. isolating said sample from said conduit, c. precompressing said sample to a predetermined volume and a predetermined pressure accompanied by a removal of excess material from said sampling chamber against said predetermined pressure, d. effecting a predetermined variation of the volume of said sample, and e. measuring the pressure in said sample at the end of said volume variation.

The invention has the advantage over the method described in U.S. Pat. specification No. 2,141,977 that there exists an absolutely unique correlation between the pressure, measured in the sampling chamber after the termination of the volume variation, and the relative air content of the sample. This unique correlation is independent of the pressure at which the air-containing material flows through the conduit, and since this pressure often may vary considerably in practice, by way of example between about 4 and 6 atmospheres absolute in conventional ice-cream freezing plants, it is of great importance that the invention permits to obtain a measuring result which is independent of the pressure in the conduit and which consequently can be used directly and without any correction for controlling the admixture of air to maintain a relative air content desired. With the measuring technique described in said U.S. specification the measured value depends, on the contrary, to a high degree on the pressure prevailing in the air-containing product at the moment when the sample is isolated from the flow passage. By comparatively simple calculations it can be shown that a given percentual variation in the volume of the sampling chamber results in a final pressure (measured as absolute pressure) which is directly proportional to the initial pressure. This means that if the absolute pressure in the flowing liquid may vary between 4 and 6 atmospheres the readings obtained with the apparatus according to the U.S. specification may deviate as much as 50% with a given relative air content in the product.

A range of variation of this magnitude obviously precludes that the reading or a signal derived from the measurement of the pressure can be used directly for controlling the admixture of air for the purpose of maintaining a desired relative air content.

The volume variation of the sample is preferably performed as an expansion since this permits to carry out a larger change in volume measured in per cent and hence also to obtain a larger change in pressure than by a compression of the sample. A compression of the sample is, however, also within the scope of the invention.

According to the invention there is also provided an apparatus for carrying out the method. The apparatus comprises a. a housing means for connecting the housing in a conduit for receiving a flow of an air containing product, b. a first and a second cylinder connected coaxially opposite one another to said housing and communicating with the interior of said housing, c. a first piston axially displaceable with a tight fit in said first cylinder, d. a second piston axially displaceable with a tight fit in said second cylinder, e. a drive mechanism connected to said pistons and arranged to displace said second piston between a first end position in which it is retracted into said second cylinder, and a second end position in which it is projected across the interior of said housing into said first cylinder to define in cooperation with said first cylinder and first piston a sampling chamber, said drive mechanism being further arranged to move said pistons axially towards one another when said second piston has entered said first cylinder, f. overflow duct means extending from said sampling chamber and containing an overflow valve, g. means for keeping said overflow valve closed when the pressure in said sampling chamber is below a predetermined magnitude, and h. means for recording the pressure in said sampling chamber.

The overflow valve may have a balanced valve member so that the valve always opens at a certain absolute pressure in the sample irrespectively of any pressure variations in the conduit. This ensures that the pressure conditions in the sampling chamber are not dependent on the pressure in the conduit during the measuring.

When the air content is determined by measuring the pressure after an expansion of the sample, this expansion and the preceding compression may be obtained with simple structural means provided the drive mechanism is rigidly connected to the second piston and is connected to the first piston through a coupling which has an axial lost motion and form part of the drive mechanism.

A sensing member for the pressure recording means may be mounted in the interior end face of the first piston, and the pressure recording means may be arranged to deliver a digital output signal which indicates whether the pressure in the sampling chamber is higher or lower than a reference value and which controls the quantity of air added to the product via an associated control system. This ensures an immediate automatic adjustment of the admixture of air in direct dependence on the measurements performed, and since the said measurements may be performed at short intervals it is possible to achieve a virtually continuous control of the air content within narrow limits.

BRIEF DESCRIPTION OF THE DRAWINGS

FIG. 1 shows a section through an embodiment of the apparatus according to the invention, transversely to the flow direction, FIG. 2 shows a longitudinal section, taken in the flow direction, through the housing of the apparatus of FIG. 1 with the two associated cylinders, whereas the pistons have been omitted for the sake of clarity.

Figure 3:
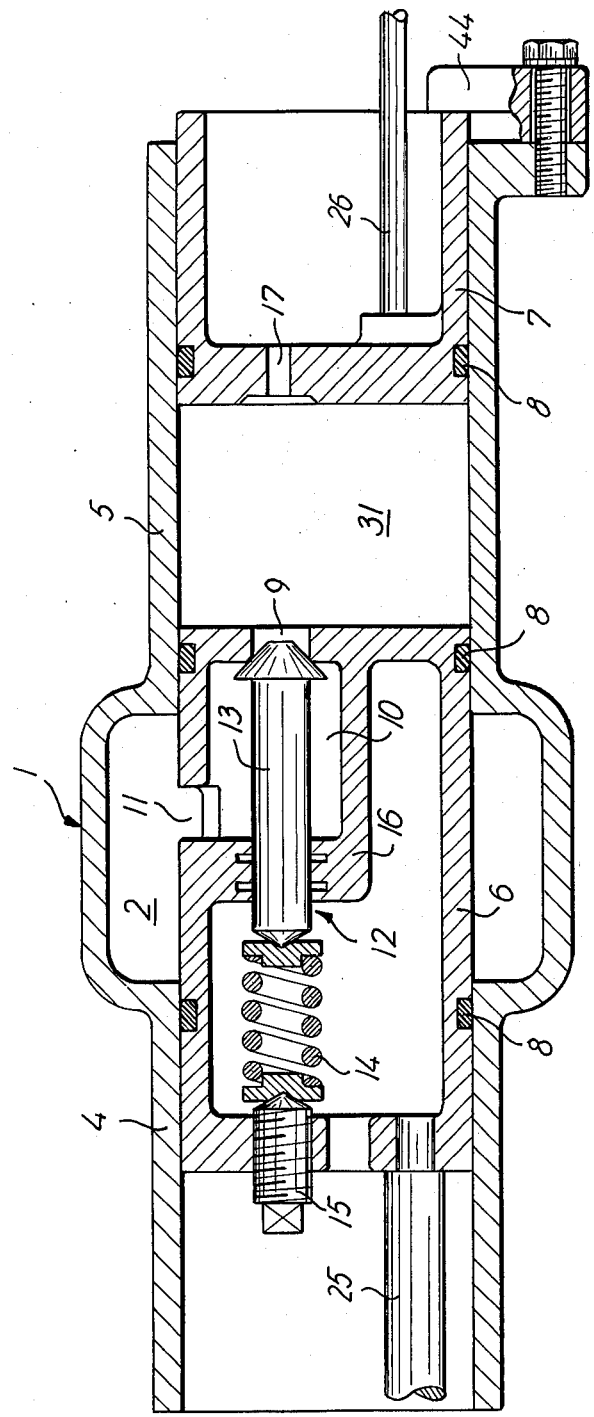
FIG. 3 shows a section on a larger scale through the housing and the two cylinders with the associated pistons in another position, the figure also showing a few structural modifications as compared to FIG. 1.

The apparatus illustrated in the drawing comprises a housing 1 having a flow chamber 2 and two branches 3 through which the housing may be connected to a pipeline for conveying ice-cream or some other product comprising a liquid phase of a higher or lower viscosity and a certain air content. While in the case of ice-cream the relatively stiff consistency of the flowing product is due to a preceding freezing, it may in other products, as for example souffle or pudding, be caused by an admixture of chemicals, such as gelatine.

The housing 1 is integral with two diametrically opposed cylinders 4 and 5, the common axis of which is at right angles to the axis through the two branches 3 and which have equal internal diameters. Each cylinder contains an axially displaceable piston, 6 and 7, respectively, which is sealed in relation to the cylinder wall by means of 0-rings or similar members 8, as shown in FIG. 3.

In its end face facing the chamber 2 the piston 6 has an aperture 9 leading to a cavity 10 which is provided internally in the piston and has an additional aperture 11 in the cylindrical surface of the piston. In the retracted position of the piston 6, which is shown in FIG. 1, the aperture 11 is covered by the wall of the cylinder 4, whereas in the second extreme position of the piston, shown in FIG. 3, said aperture is located within the chamber 2 of housing 1. The aperture 9 is controlled by a spring-loaded overflow valve 12 having a valve member 13 with a conical head which cooperates with a valve seat surrounding the aperture 9 and a shank which is guided in the piston 6 and has the same diameter as the aperture 9. The valve member 13 is biased by a compression spring 14, the force of which can be adjusted by means of an adjusting screw 15. In the wall 16 of the piston 6, in which the shank of the valve member 13 is guided, there is provided a sealing means for the shank, such as the labyrinth sealing shown in FIG. 3.

In its end face facing the piston 6 the piston 7 has an aperture 17 which via a conduit 18 shown diagrammatically in FIG. 1 is connected to a pressure gauge 19 which consequently indicates the pressure in the space which is at any time defined between the opposed end surfaces of the two pistons. The aperture 17 will normally be closed towards the said space by means of a diaphragm (not shown) or alternatively a pressure sensor or transducer which delivers an electric signal representing said pressure may be mounted in the aperture 17.

The housing 1 is secured to a support 20 (see FIG. 1) which also carries a pneumatic or hydraulic ram comprising a cylinder 21 with an associated piston 22 having a piston rod 23 extending parallel to the common axis of the two cylinders 4 and 5. To the piston rod 23, an arm 24 is secured which at its free end is secured to a piston rod 25 projecting rearwardly, that is to say to the left, from the piston 6. The piston 7 has an outwardly projecting piston rod 26 which is secured to an arm 27 which is guided slidingly on the piston rod 23. Outside the arm 27, a stop ring 28 is secured to the piston rod 23.

Two fluid lines 29 and 30 are connected to the ends of the cylinder 21, so that when pressurized fluid is supplied through one line and fluid is exhausted to a tank (not shown) through the other line the piston 22 may be displaced between its two extreme positions shown in FIG. 1 in full lines and dotted lines, respectively.

In the first mentioned extreme position, the internal end faces of both pistons 6 and 7 are flush with the walls of chamber 2 and the arm 27 abuts on stop ring 28. In this position, which the components of the apparatus take up between two measurements, an unobstructed flow of ice-cream or other product may thus take place through an external conduit connected to the branches 3 of housing 1.

When pressurized fluid is supplied through line 29 the piston 22 is moved to its second extreme position. The piston rod 23 directly carries the piston 6 secured thereto along towards the right, and when piston 22 is at the right-hand end of the cylinder 21 piston 6 takes up the position shown in FIG. 3. Assuming that a positive pressure prevails in the product flowing through chamber 2, this pressure will also carry piston 7 along towards the right, and it appears from FIG. 3 that the movement of the two pistons will cause a transfer of a quantity of the product from chamber 2 to a chamber 31 defined in the cylinder 5 between the pistons. Shortly before the termination of the movement of piston 22, when piston 6 has entered the cylinder 5, a pre-compression of the sample in chamber 31 occurs, in that the extreme end of piston rod 26 abuts on a stationary abutment or stop 32 secured to an arm 33 projecting upwardly from support 20. After this, the piston 7 remains stationary while the piston 6 performs its final movement to the right.

At the same time as the piston rod 26 is stopped by the stop 32, a contact piece 34, which is secured to arm 27, but electrically insulated from the arm, establishes an electric connection between two contact pieces 35 which are insulated from each other and are mounted on arm 33 and which through electric lines 36 are connected to a control unit 37 not described in detail. Via electric lines 38 the control unit is connected to the pressure gauge 19 which — as mentioned above — is arranged for indicating the pressure acting on the left-hand end face of the piston 7 and for delivering a digital signal to the control unit 37. The signal may for example have the value 1, when said pressure is higher than a predetermined reference valve, and the valve 0 when the pressure is lower than the reference valve. Via a diagrammatically indicated control line 39 the control unit 37 delivers an order signal to a motor 40 which controls the degree of opening of a modulating valve 41 in a conduit 42 which connects a compressed-air vessel 43 to an ice-cream freezer (not shown) the outlet of which for the frozen cream is connected to one of the branches 3 of the housing 1.

The spring 14 is adjusted to bias the valve member 13 of valve 12 with such a closing force that the valve opens to permit ice-cream to flow from sampling chamber 31 to housing 1 when the pressure in chamber 31 assumes a predetermined absolute value which is higher than the maximum pressure which under normal operation may prevail in chamber 2. The opening of the valve occurs during the above-mentioned final phase of the movement of piston 22 to the right, during which the sample in chamber 31 is compressed because piston 7 is stationary. Since, as mentioned above, the diameter of the shank of valve member 13 is equal to the diameter of the aperture 9, the valve is completely relieved of the pressure prevailing in the chamber 10 in its closed position so that, irrespective of the pressure in the ice-cream flowing through chamber 2, it will always open at a certain absolute pressure. In this connection it is permissible to neglect variations, if any, of the atmospheric pressure acting on the outer end of the valve member.

When piston 22 is in its right-hand extreme position, and when valve 12 has closed again after the pressure in chamber 31 determined by the bias of the spring 14 has been established working fluid is supplied to cylinder 21 through line 30 and piston 22 moves to the left. During this movement, piston 7 initially remains stationary due to the positive pressure in chamber 31 acting on its left-hand face, but at the moment when the stop ring 28 contacts arm 27 the piston starts following piston 6 to the left. Up to this moment, the sample present in chamber 31 expands and the pressure in the chamber drops. It will be apparent that the drop in pressure becomes the greater the smaller the air content of the ice-cream, that is to say its swelling degree. The pressure gauge 19 continuously records the pressure prevailing in chamber 31, and at the moment when the expansion is terminated and piston 7 is carried along by stop ring 28, the electric connection between the two contact pieces 35 is also interrupted.

The control unit 37 is designed such that this interruption of the current causes the delivery of a control signal via line 39 to the motor 40 corresponding to the digital signal emitted from the pressure gauge via lines 38. The duration of the control signal to motor 40 is determined by a (preferably adjustable) timer incorporated in unit 37, and dependent on whether the digital signal is 1 or 0, that is to say whether the pressure in the ice-cream at the termination of the expansion deviates from the preset reference value in one or the other direction, motor 40 adjusts valve 41 to compensate for the deviation measured by increasing or decreasing the rate of air flow through valve 41 and conduit 42 connected to the freezer.

The digital measuring signal from pressure gauge 19 may for example be produced by means of two contacts, which in the pressure gauge are connected to one each of the two lines 38 and which are short-circuited when the pressure measured deviates in one direction from the reference value, while in the case of a deviation in the opposite direction they are insulated from each other.

Apart from a modification in the details of the pistons 6 and 7, the embodiment illustrated in FIG. 3 differs from that shown in FIG. 1 in that the outward movement of piston 7 is stopped by an abutment 44 which is secured directly to the cylinder 5. It will be apparent, however, that many others of the details shown may be modified within the scope of the invention. The piston 6 might, by way of example, be connected directly to the piston rod of a fluid ram, and in that case a coupling having an axial lost motion might be provided directly between the opposed end faces of the pistons. The measurement of the swelling degree or air content may also be performed in other ways than that described, for example by measuring the dielectricity constant of the sample trapped between the two pistons at a determined pressure or by measuring the permeability of the sample to ultrasonic waves or electromagnetic radiation. When the measuring apparatus is coupled directly to apparatus for controlling the admixture of air as described, it may comprise a timer which determines the (preferably adjustable) duration of the period between two successive measurements and the resulting adjustments of the air supply rate.

Since the samples withdrawn for measuring are returned to the conduit after the measuring operation, the size of the samples may be chosen solely out of regard to the accuracy required, that is to say rather large in practice, so that residual material, if any, left on the walls of the sampling chamber from preceding measurements will only have a minimum influence on the result of the measurement.

What we claim is:

1. Apparatus for determining the relative air content in a product flowing through a conduit in the form of air containing liquid or cream, said apparatus comprising:
   a. a housing having means for connecting the housing in a conduit for receiving a flow of the product,
   b. a first cylinder and a second cylinder connected coaxially opposite one another to said housing and communicating with the interior of said housing,
   c. a first piston axially displaceable with a tight fit in said first cylinder,
   d. a second piston axially displaceable with a tight fit in said second cylinder,
   e. a drive mechanism means connected to said pistons and arranged to displace said second piston between a first end position in which it is retracted into said second cylinder, and a second end position in which it is projected across the interior of said housing into said first cylinder to define, in cooperation with said first cylinder and said first piston, a sampling chamber, said drive mechanism means being further arragned to move said pistons axially towards one another when said second piston has entered said first cylinder,
   f. overflow duct means extending from said sampling chamber and containing an overflow valve,
   g. means for keeping said overflow valve closed when pressure in said sampling chamber is below a predetermined magnitude, and
   h. means for recording the pressure in said sampling chamber.

2. An apparatus as claimed in claim 1, wherein said overflow duct means connects said sampling chamber with the interior of said housing.

3. An apparatus as claimed in claim 2, wherein said second piston has a cylindrical surface, said overflow duct means and said overflow valve are provided in said second piston, and the downstream end of said duct means opens into said cylindrical surface of said second piston.

4. An apparatus as claimed in claim 1, wherein said overflow valve includes a balanced valve member.

5. An apparatus as claimed in claim 1, including adjustable spring means biasing said overflow valve towards its closed position.

6. An apparatus as claimed in claim 1, wherein said drive mechanism means is rigidly connected to said second piston and is connected to said first piston through coupling means of the axial lost-motion type.

7. An apparatus as claimed in claim 6, further including stop means for determining an outer end position of said first piston relative to said housing.

8. An apparatus as claimed in claim 1, further comprising sensing means mounted in the interior end face of said first piston and connected to said means for recording pressure.

9. An apparatus as claimed in claim 8, including controlled valve means and a control system, and wherein said means for recording pressure is arranged to deliver, via said control system, a digital output signal indicating whether pressure in said sampling chamber is higher or lower than a reference value to control valve means for adjusting air content in said product.

10. An apparatus as claimed in claim 1, wherein said drive mechanism means comprises a drive mechanism means for moving said pistons axially towards one another to a position in which said sampling chamber has a predetermined volume, after said second piston has entered said first cylinder, and for moving said pistons subsequently relative to one another to effect a predetermined variation of the volume of said sampling chamber.

* * * * *